United States Patent [19]

Schechter et al.

[11] Patent Number: 5,058,600
[45] Date of Patent: Oct. 22, 1991

[54] GRAPHICAL READOUT OF LARYNGOTRACHEAL SPECTRA AND AIRWAY MONITOR

[75] Inventors: Gary L. Schechter, Norfolk; Robert F. Coleman, Virginia Beach, both of Va.

[73] Assignees: Center for Innovative Technology, Herndon; Eastern Virginia Medical School of the Medical College, Norfolk, both of Va.

[21] Appl. No.: 461,675

[22] Filed: Jan. 8, 1990

[51] Int. Cl.$^5$ .............................................. A61B 5/08
[52] U.S. Cl. .................................... 128/716; 128/720
[58] Field of Search ......................... 128/716, 719, 720

[56] References Cited

U.S. PATENT DOCUMENTS

| | | |
|---|---|---|
| 3,771,792 | 9/1988 | Seale . |
| 3,990,435 | 11/1976 | Murphy ................... 128/716 |
| 4,306,567 | 12/1981 | Krasner . |
| 4,379,460 | 4/1983 | Judell . |
| 4,422,458 | 12/1983 | Kravath . |
| 4,450,527 | 5/1984 | Sramek . |
| 4,452,252 | 6/1984 | Sackner . |
| 4,456,015 | 6/1984 | Sackner . |
| 4,597,394 | 7/1986 | Sackner . |
| 4,646,754 | 3/1987 | Seale . |
| 4,769,639 | 1/1989 | Snow ................... 128/719 |
| 4,836,218 | 6/1989 | Gay . |
| 4,940,058 | 7/1990 | Taff ..................... 128/716 |

FOREIGN PATENT DOCUMENTS

0061014 9/1982 European Pat. Off. ............ 128/720

OTHER PUBLICATIONS

*Spectral Characteristics of Normal Breath Sounds*, Gavriely et al., 1981, Journal of the American Mysiological Society.

H. John Zarra, Respiratory Rate Monitor Using an Audio Pick-Up, Nov. 1979, pp. 49-52, from Conference-Proceedings of 7th New Engineering Bioengineering Conference.

Hirschberg, Jeno, "Acoustic Analysis of Pathological Cries, Striders and Coughing Sounds in Infancy", Int. J. Fed. Otorhinolaryngol. 2:287-300, 1980.

Gray, Lincoln, James C. Denny, III, Hugo Caravajal, and Robert Johnsdoerfer, "Fourier Analysis of Infantile Stridor; Preliminary Data", Int. J. Ped. Otorhinolaryngol. 10:191-199, 1985.

(List continued on next page.)

*Primary Examiner*—Kyle L. Howell
*Assistant Examiner*—Robert L. Nasser, Jr.
*Attorney, Agent, or Firm*—Whitham & Marhoefer

[57] ABSTRACT

A laryngotracheal airway spectra readout and monitor uses one or more miniature accelerometers placed on the outside of the neck of a patient to generate acoustic signals of patterns of breathing. The miniature accelerometers act as contact microphones which are sensitive to the physical vibration of breathing noise but otherwise insensitive to ambient and environmental noise. The acoustic signals are processed using Fast Fourier Transform (FFT) or other suitable acoustic analysis to generate a digitized spectra which may be printed out or recorded for later diagnostic analysis. The printoputs are in the form of a calibrated and normalized graphic readout which can be read by trained physicians or technicians in much the same way as EKGs. The digitized spectra is analyzed by comparing identified parameters of the spectra with a database of known parameters of normal and abnormal airways. Decision algorithms are then used to make diagnoses based on the comparison with the stored normal and abnormal parameter data, and the results of the diagnoses are presented graphically, either on screen or printed or both. Audible and/or visual alarms may also be generated if predetermined conditions are detected. In addition, records of current breathing analysis are stored and can be compared as a function of time to ascertain improvement or deterioration of a patient's condition.

11 Claims, 5 Drawing Sheets

OTHER PUBLICATIONS

Leiberman, Alberto, Arnon Cohen and Ashertal, "Digital Signal Processing of Stridor and Snoring in Children", Int. J. Ped. Otorhinolaryngol., 12:173–185, 1986.

Charbonneau, G., J. L. Racfineux, M. Sudraud, and E. Tuchais, "An Accurate Recording System and Its Use in Breath Sounds Spectral Analysis", J. Appl. Physiol.: Respirat. Environ. Exercise Physiol. 55(4):1120–1127, 1983.

Gavriely, Noam, Yoram Palti, Gideon Alroy, and James B. Grotbherg, "Measurement and Theory of Wheezing Breath Sounds", J. Appl. Physiol:Respirat. Environ. Exercise Physiol. 57(2):481$\propto$492, 1984.

B.) Coleman, R. F., "Comparison of Microphone and Neck Mounted Accelerometer Monitoring of the Performing Voice", Invited Paper, Sixteenth Symposium, Care of the Professional Voice, Lincoln Center, New York, Jun. 1987.

C.) Coleman, R. F., "Epidermal Vibration Responses to Different Voice Modes", Invited Paper, Seventeenth Symposium, Care of the Professional Voice, Lincoln Center, New York, Jun. 1987.

Tatum, S., Coleman, R., and Schecter, G., "Accoustic Analysis of Airway Obstruction in a flexible Model", Poster Presentation, American Academy of Otolaryngology–Head and Neck Surgery, Washington, D.C., Sep. 1988.

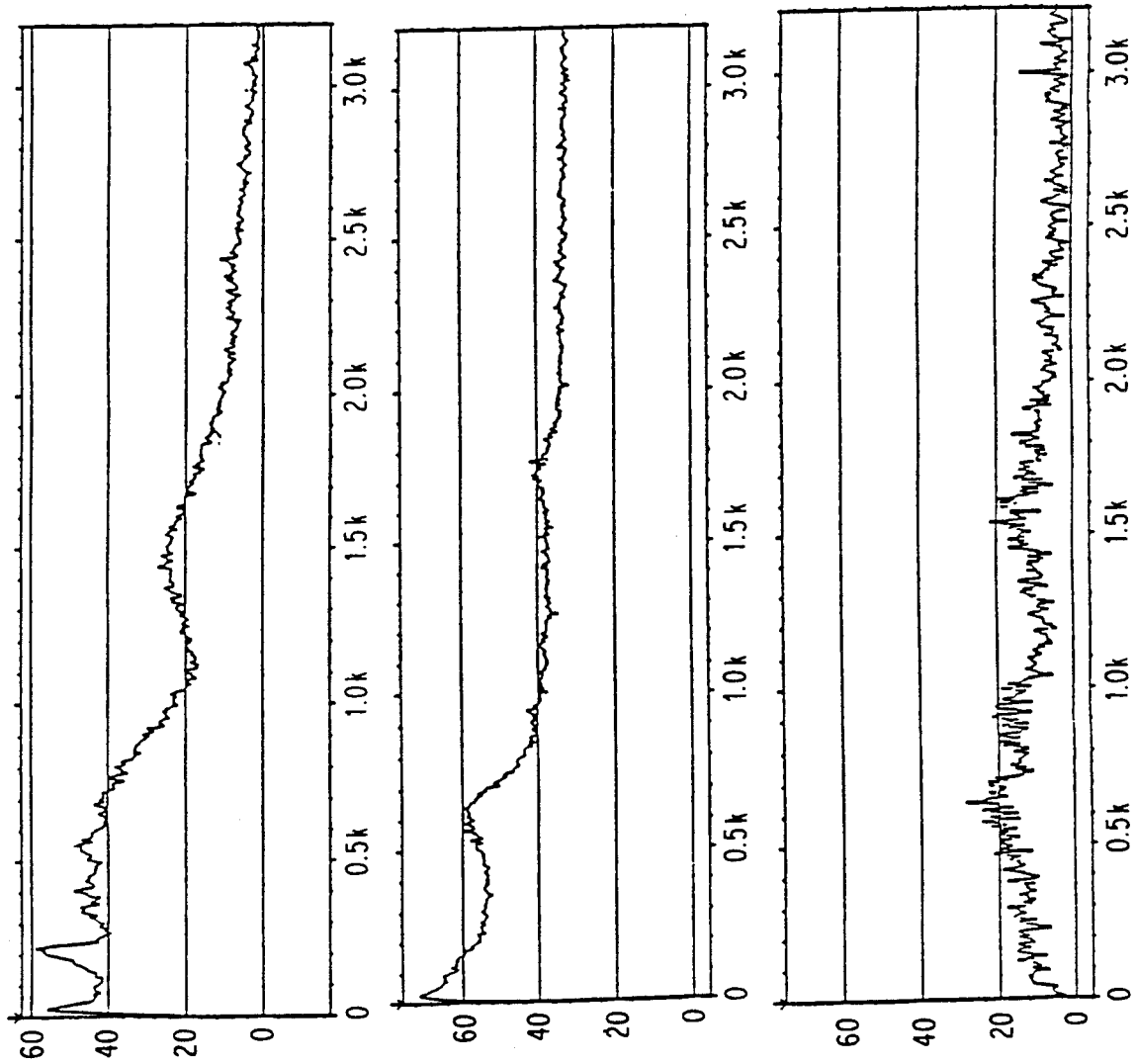

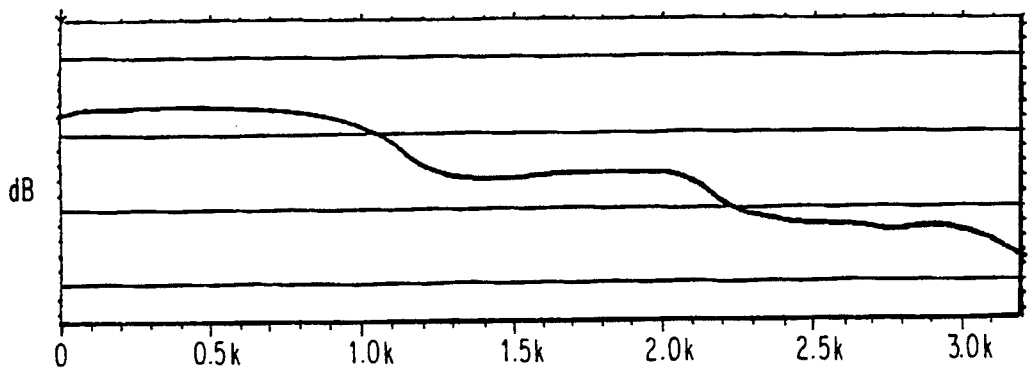
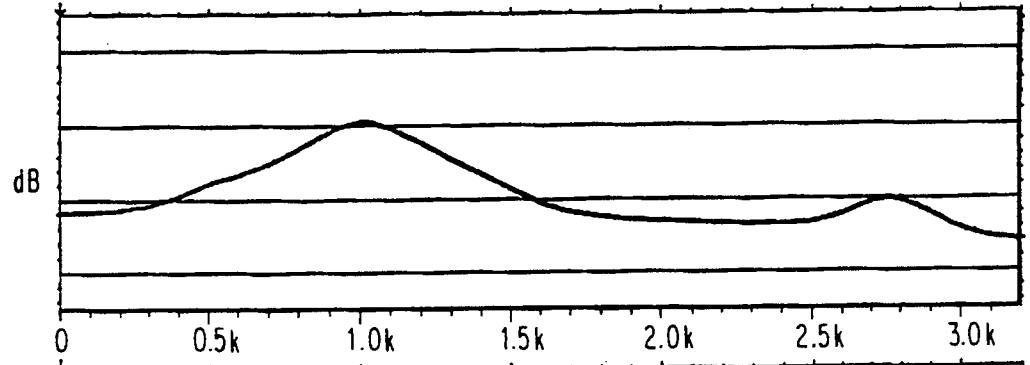
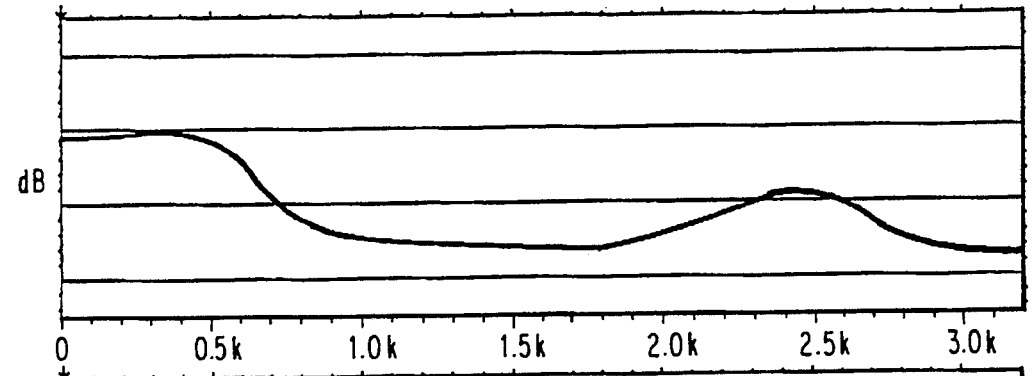
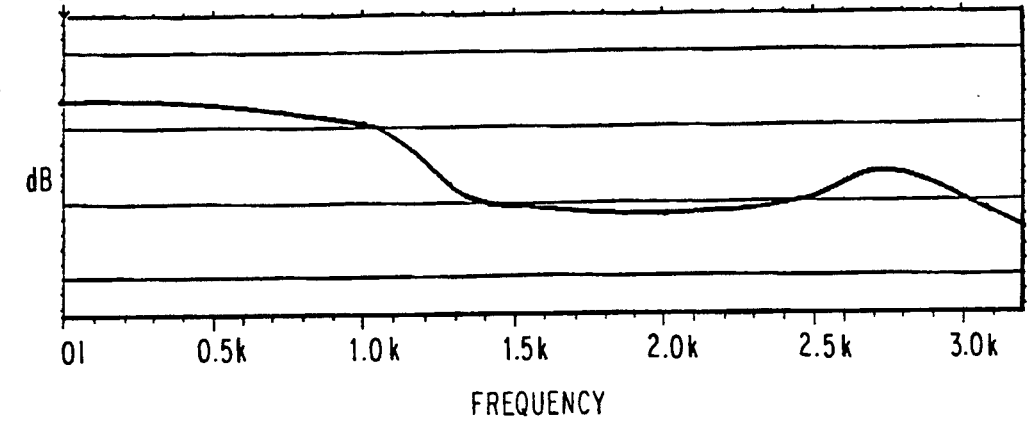
FREQUENCY

GRAPHICAL READOUT OF LARYNGOTRACHEAL SPECTRA AND AIRWAY MONITOR

DESCRIPTION

Background of the Invention

1. Field of the Invention

The present invention generally relates to generating calibrated and normalized graphic readouts of laryngotracheal spectra and the non-invasive monitoring of adult and pediatric airways for the purpose of determining the location and degree of an airway obstruction and, more specifically, to a method and apparatus for the acoustic signal generation, processing and analysis of human airway noise to make rapid and accurate diagnoses of the location and degree of airway obstructions.

2. Description of the Prior Art

Upper airway obstruction is a medical emergency faced by clinicians on a daily basis. Pediatric airway compromise is an often life threatening situation requiring expedient diagnosis and treatment. Endoscopy has been and continues to be the mainstay for management of a compromised airway, but it is an invasive procedure often requiring general anesthesia. Moreover, endoscopy has a potential side effect of tissue swelling as a reaction to the introduction of the invasive fiber optic bundle. Other methods of observation, including radiographic studies, are time consuming, costly, and have other potential side effects such as or resulting from exposure to radiation.

Clinicians have been relying on sound for evaluation of the airways for centuries. Acoustic evaluations of upper airways usually consist of stethoscope auscultation and gross determinations by the clinician at the bedside. No clinically applicable method is presently available to monitor airway obstruction by acoustic analysis. Only recently, however, have sophisticated acoustical recording and measurement techniques been applied to clinical evaluations. Hirschberg reported in "Acoustic Analysis of Pathological Cries, Stridors and Coughing Sounds in Infancy", *Int. J. Ped. Otorhinolaryngol.*, 2:287–300, 1980, the spectrographic analysis on the pathologic cries, stridors and coughing sounds of 180 infants. In a more advanced analysis, using Fast Fourier Transform (FFT) techniques, Gray et al. reported in "Fourier Analysis of Infantile Stridor: Preliminary Data", *Int. J. Ped. Otorhinolaryngol.*, 10:191–199, 1985, their investigation of stridor in a group of children and outlined four distinct acoustical patterns that describe pathologic states. Leiberman et al. reported in "Digital Signal Processing of Stridor and Snoring in Children", *Int. J. Ped. Otorhinolaryngol.*, 12:173–185, 1986, a combined Fourier analysis with computer modeling of the pediatric airway to ascertain the site and degree of obstruction in five children with stridor.

While these investigators have reported using acoustic analysis, none have established a basis for a specific apparatus that is dedicated to the task. Previous acoustic research studies have used normal microphones to record airway sounds, with resultant contamination of the signal by ambient noise in the examination room.

What is needed is a noninvasive, conveniently performed and standardized technique of airway evaluation in patients convenient for bedside use in a continuous mode and independent of examiner bias.

SUMMARY OF THE INVENTION

It is therefore one object of the invention to provide a calibrated and normalized readout of a patient's laryngotracheal airway spectra which can be read by trained physicians or technicians to evaluate the patient's condition.

It is another object of the present invention to provide a non-invasive technique for the acoustical evaluation of upper airway obstruction which may be operated continuously to monitor a patient's condition.

It is another object of the invention to provide non-invasive system that is capable of the rapid and accurate diagnoses of the location and degree of obstruction in the upper airway of a patient without exposing the patient to any undesirable side effects.

According to the invention, acoustic signals of airway noise are picked up (i.e., transduced) using one or more miniature accelerometers placed on the outside of the neck of a patient. The miniature accelerometers act as contact microphones which are sensitive to the physical vibration of breathing noise but otherwise insensitive to ambient and environmental noise. The acoustic signals are processed using Fast Fourier Transform (FFT) or other suitable acoustic analysis to generate a digitized spectra which may be recorded for later diagnostic analysis. The digitized spectra is analyzed by comparing identified parameters of the spectra with a database of known parameters of normal and abnormal airways. Decision algorithms are then used to make diagnoses based on the comparisons with the stored normal and abnormal parameter data, and the results of the diagnoses are presented graphically, either on screen or printed or both. Audible and/or visual alarms may also be generated if predetermined conditions are detected. In addition, records of current breathing analysis are stored and can be compared as a function of time to ascertain improvement or deterioration of a patient's condition.

BRIEF DESCRIPTION OF THE DRAWINGS

The foregoing and other objects, aspects and advantages will be better understood from the following detailed description of a preferred embodiment of the invention with reference to the drawings, in which:

FIGS. 3A to 3C are two-dimensional graphs of the spectral analysis of an adult with acute laryngotracheitis;

FIGS. 4A to 4D are idealized templates corresponding to different obstruction locations.

DETAILED DESCRIPTION OF A PREFERRED EMBODIMENT OF THE INVENTION

Figure 1:
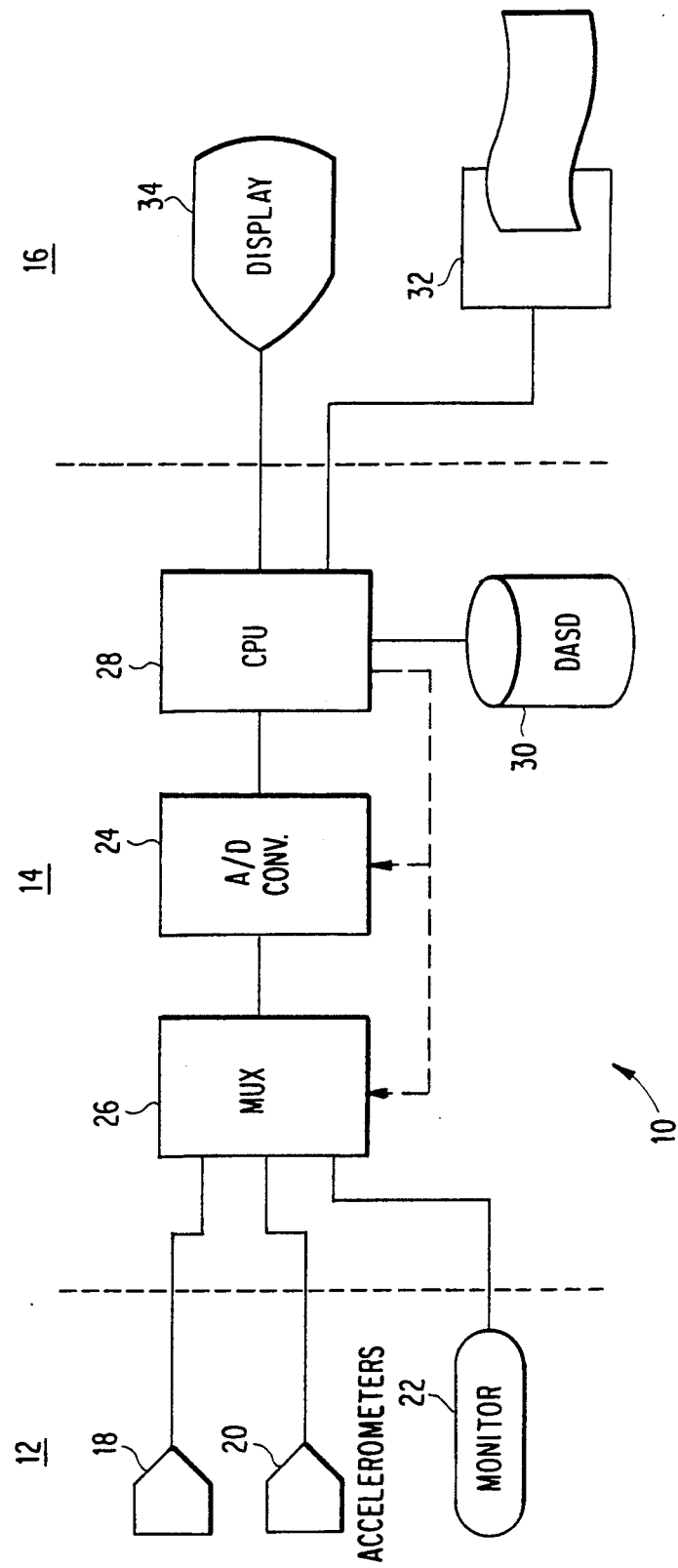
FIG. 1 is a general block diagram showing the basic components of the laryngotracheal airway monitor according to the invention.

Referring now to the drawings, and more particularly to FIG. 1, there is shown in block diagram the components of a laryngotracheal monitor 10 according to the invention. The monitor comprises three principal parts: the sensing transducer 12, a central processor 14 and a readout device 16.

The transducer 12 consists of at least one and preferably a pair of accelerometers 18 and 20 which are placed on the outside surface of the neck of a patient to generate electrical signals to the central processor 14 corresponding to the acoustic vibratory pattern of the patient's breathing. Accelerometers are used as the transducers because they are in effect "contact microphones" sensing physical vibration rather than sound waves per se. The advantage of these transducers is that they have a very high signal-to-noise (S/N) ratio, meaning that the airborne noise from the typically noisy examination, operating, clinic, or intensive care room is not picked up by these devices. In addition to inputs from the accelerometers 18 and 20, an input from a "Respitrace" pulmonary monitor 22 or other device is provided to the central processor 14. The purpose of this input is to tell the processor which phase of a cycle (inhalation-exhalation) it is analyzing.

For some conditions, the phase of the respiratory cycle in which maximum noise occurs is highly indicative of the location of airway obstruction. Gross differentiation of obstruction above and below the larynx can often be made by observing such cycle-dependent relationships. A supra-laryngeal obstruction will ordinarily produce maximum noise upon inspiration, while the reverse is true for obstructions below the larynx. The "Respitrace" or other pulmonary monitor can indicate the phase of a respiratory cycle by monitoring changes in thoracic volume, with a consequent change in outer thoracic size which is monitored by the pulmonary device.

The central processor 14 includes several components. The first of these is an analog-to-digital converter (A/D) 24 which is connected via a multiplexer 26 to digitize the analog signals from the transducers 18 and 20 and from the monitor 22. A separate A/D converter for each input may be used thereby eliminating the need for a multiplexer. The A/D converter 24 and the multiplexer 26 are controlled by a central processing unit (CPU) 28 which temporarily stores the digitized inputs in internal registers (not shown). The CPU 28 may be, for example, a Compaq or similar personal computer (PC) which operates with the Interactive Analysis System (ILS) software from Signal Technology, Inc. This advanced acoustic software package enables analysis of frequency, time, amplitude, and spectral characteristics of acoustic signals. The data is analyzed using FFT algorithms which provide precise definition of signal frequency and amplitude at either evenly spaced increments of time (in the case of the ILS routines) or an average of one hundred consecutive FFTs which are in effect compressed into one cumulative spectrum (in the case of a Bruel and Kjaer 2034 Spectrum Analyzer).

The use of either the ILS software or the Bruel and Kjaer 2034 Spectrum Analyzer is not necessary, these being examples of software and devices currently in use in our laboratory. Broadly speaking, what is required is hardware and/or software that enables the acquisition of (1) an averaged FFT spectrum and (2) a three-dimensional or "waterfall" spectrum consisting of successive FFTs over time. These outputs (i.e., the averaged FFT and three-dimensional FFTs) provide the first product of our device; that is, a printout of the spectral pattern of airway sounds. As will be described hereinafter, this product can be subjected, in digital form, to further pattern recognition routines; however, this product has utility in and of itself. More specifically, the printout produced is a calibrated and normalized graphic readout which may be read by trained physicians or technicians in much the same way that EKGs are read.

Returning now to FIG. 1, a database 30, here represented by a Direct Access Storage Device (DASD), is accessed by the CPU 28 to compare the processed data with acoustic parameters stored in the database. The database includes a library of parameters stored as a series of algorithms or templates and cataloged according to age, height, weight, sex and medical condition including blood pressure, oxygen saturation level, and the like. The CPU 28 employs a decision algorithm, which may be implemented as an expert system, to make diagnoses of the location and degree of an airway obstruction. The CPU 28 also stores in the database 30 the contemporary data for later comparison with updated input to determine changes in the acoustic spectra which can then be related to physical changes in the patient's airway.

The readout device takes the form of a printer or chart recorder 32 which prints out a permanent record of the analyzed data. In addition, the readout device may include a display screen 34 on which a graphical display is generated showing the analyzed data. The output may be in numerical form, although a graphical readout is preferred. The graphical readout may optionally be augmented by numerical data. Audible and/or visual alarms may also be generated by the CPU 28 if predetermined conditions are detected.

Figure 2A:
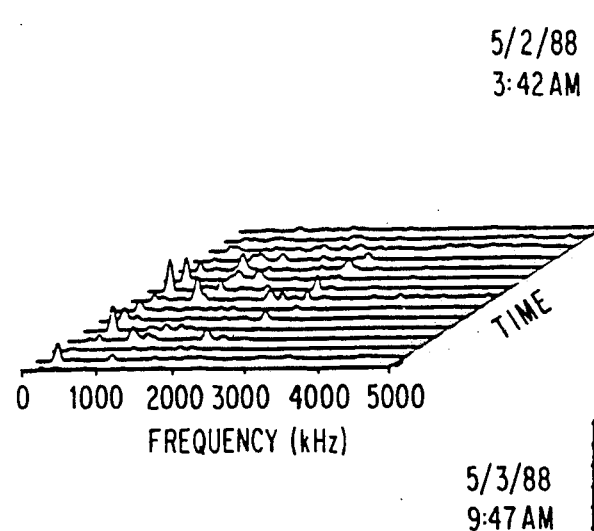
FIGS. 2A to 2D are three-dimensional displays of acoustic pattern analyzed by Fast Fourier Transform showing the acoustic history of a child with a sub-glottic hemangioma.
Figure 2B:
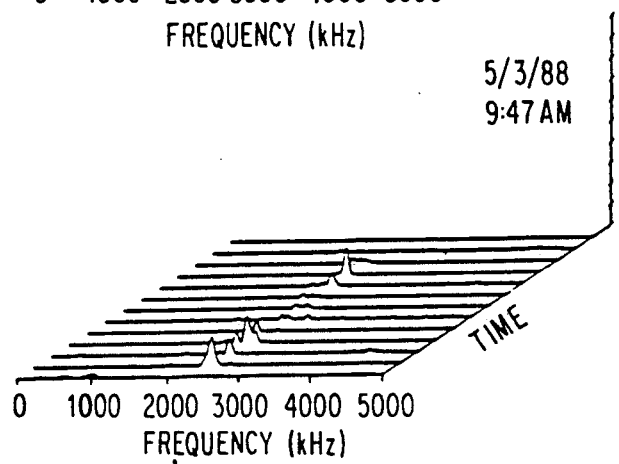
Figure 2C:
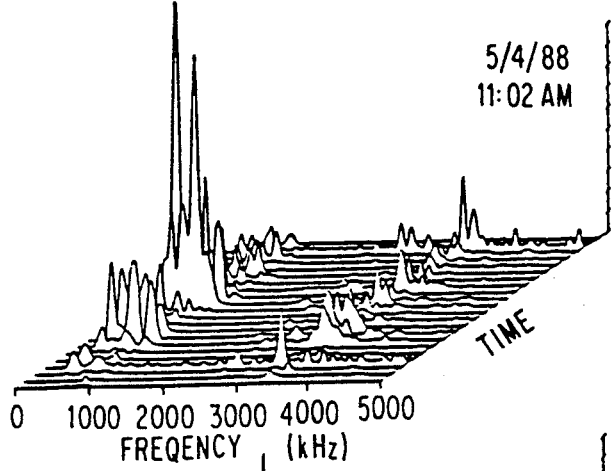
Figure 2D:
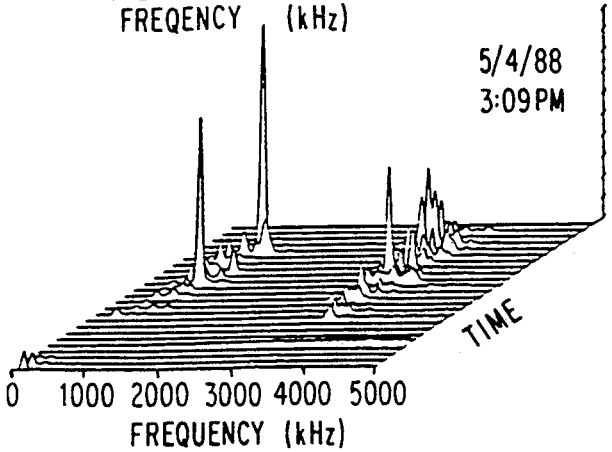

FIGS. 2A to 2D show a series of three-dimensional FFTs from a single patient. This record is of a three month old infant who was admitted in acute respiratory distress due to a large subglottic hemangioma. FIG. 2A is a breathing sample taken immediately following removal (extubation) of a breathing tube in her airway. FIG. 2B, obtained the next morning, shows continued improvement in her breathing pattern in response to high-dose steroids. FIG. 2C, taken approximately twenty-six hours later, indicates a recurrence of airway obstruction with generalized increase in noise components, and maximum noise occurring at the beginning of the expiratory phase of the breathing cycle (in the middle of the figure). FIG. 2D shows improvement in the overall noise level, but with brief "spikes" of sound (stridor) upon exhalation.

FIGS. 3A to 3C show an averaged (long-term) FFT analysis of an adult female admitted to an intensive care unit with severe tracheobronchitis. FIG. 3A demonstrates "spikes" at approximately 50 Hz and 200 Hz which is typical of a true stridor. In addition, noise components are primarily in the lower portion of the spectrum, indicating a laryngeal or sub-laryngeal obstruction. FIG. 3B illustrates an improvement in the airway, with a diminution of lower frequency noise and elimination of the stridor "spike" seen at 200 Hz in FIG. 3A. Low frequency components still persist in FIG. 3B, however, suggesting continued airway compromise. FIG. 3C, obtained two days after FIG. 3B, demonstrates a marked overall reduction in noise level to the point that this sample could be identified as normal.

FIGS. 2A to 2D and FIGS. 3A to 3C contrast the use of a three-dimensional spectral display with a long-term average, respectively. Both types of displays have unique advantages. The three-dimensional spectra of FIGS. 2A to 2D, for example, are useful to indicate the respiratory cycle phase in which maximum noise occurs, in this case a sublaryngeal obstruction. FIGS. 3A to 3C, on the other hand, represents a long-term average of several respiratory cycles, and so provides a record of the main noise components over time. The sharp, brief spikes in FIG. 2D would not have been as pronounced in an average display. Both types of displays are useful in detecting the location and degree of airway obstructions.

The spectral analyses shown in FIGS. 2A to 2D and FIGS. 3A to 3D are illustrative of the analyses that may be obtained using commercially available pattern analysis and recognition software such as the ILS software available from Signal Technology, Inc. The present invention is comprised of two main parts: The first consists of an accelerometer, pulmonary monitor, and an FFT analysis array to furnish readouts which are available to the clinician. These readouts include three-dimensional and long-term spectral analyses of the type generally shown in FIGS. 2A to 2D and FIGS. 3A to 3C, respectively. These are available in a dedicated instrument which will automatically print out the results in an appropriate standardized format, in much the same manner as EKGs are clinically available. The second part of the invention is an automated pattern recognition section which produces a "best-fit" pattern recognition decision. This second part is described in more detail in the following discussion.

The algorithms used by the invention for pattern recognition may best be conceptualized as a series of templates fitted to a spectrum whose parameters are frequency, amplitude and time. FIGS. 4A to 4D provide an illustration of this concept. The four spectra of these figures are idealized curves derived from a preliminary set of human recordings. FIG. 4A shows an oropharyngeal obstruction; i.e., enlarged palatal and lingual tonsils. FIG. 4B shows a supra-glottal obstruction; i.e., epiglottis. FIG. 4C shows a glottal obstruction; i.e., vocal cord tumor or edema. FIG. 4D shows a sub-glottal obstruction; i.e., a subglottal hemangioma, stenosis, or coup.

An examination of each of the idealized curves shown in FIGS. 4A to 4D reveals a distinctive pattern. In FIG. 4A, there is a "stair-step" function with decreasing amplitude as frequency increases. In FIG. 4B, there is a peak frequency located between 750 and 1200 Hz with a secondary peak located at a relatively high frequency. In FIG. 4C, there is a predominant region of energy located below 500 Hz., a marked "valley" or region of decreased amplitude, and a secondary, relatively broadband peak at higher frequencies. In FIG. 4D, there is a marked broadband region of energy extending from near 0 Hz with a secondary, broadband peak in the region 2500 to 3000 Hz. Broadly stated, the invention uses templates such as these to analyze the monitored spectra from a patient and produce accurate and reliable diagnoses.

The variables analyzed include amplitude, peaks in the frequency continuum and the bandwidth of the peaks. By amplitude, what is meant is the total RMS (root mean squared) amplitude. As an obstruction increases, the total noise, measured as RMS amplitude over an entire spectrum, will increase until a point is reached where noise falls off abruptly due to lack of respiratory drive. Given two samples, the one with the greater RMS amplitude will represent greater obstruction. The frequency location of a peak or a series of peaks helps to indicate where an obstruction is located. A prominent peak at a low frequency region indicates a lower resonance point and a larger physical volume of a resonator, characteristic of a subglottal obstruction. Similarly, a series of closely spaced peaks in the spectrum indicates a resonator with a low first resonance and a longer physical dimension, also characteristic of a subglottic obstruction. In general, the narrower the bandwidth of a given spectral peak, the greater the degree of obstruction which will be present. "Stridor" is essentially a whistle-like sound, represented by a new pure tone (single frequency) or series of frequencies.

Figure 5:
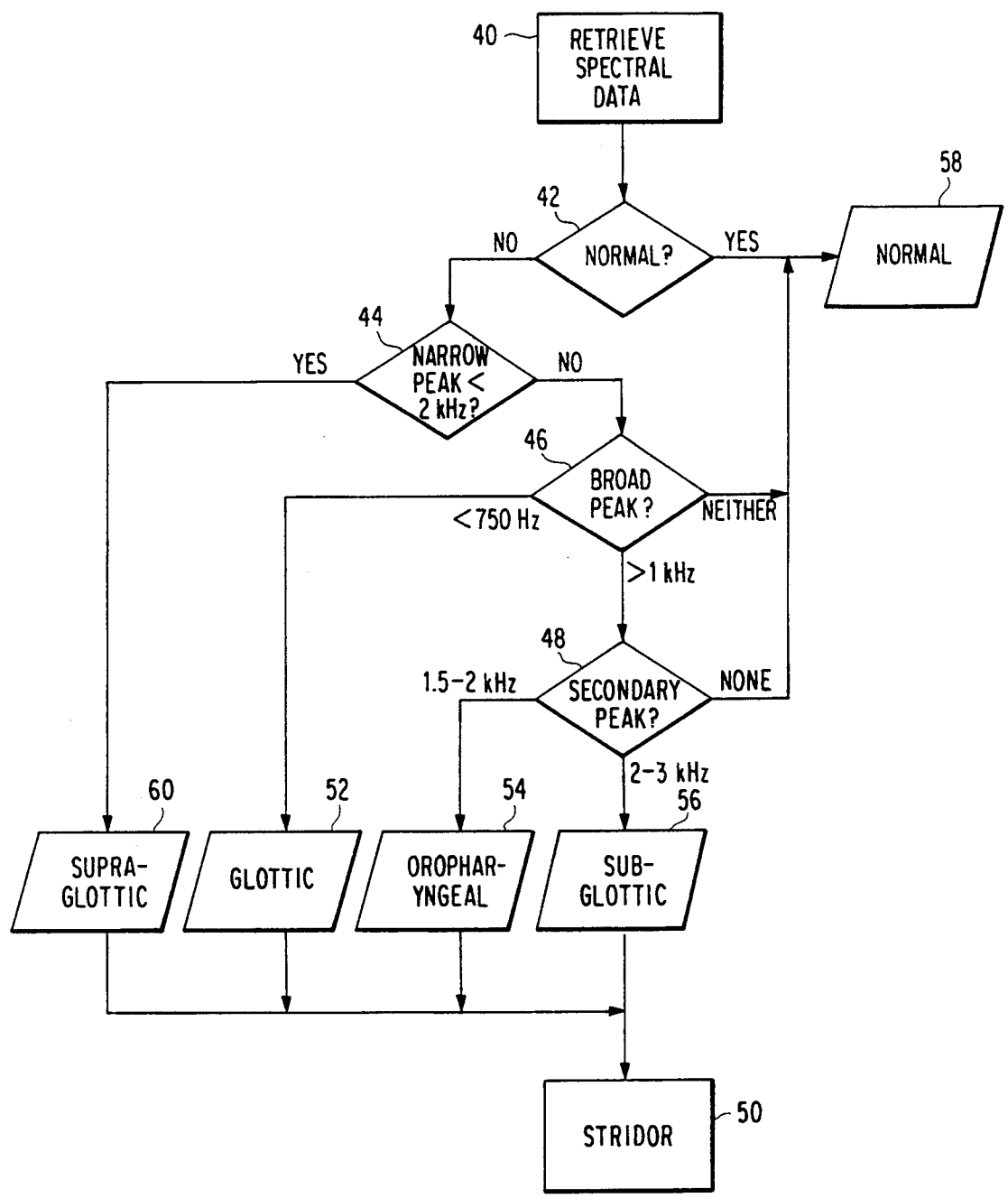
FIG. 5 is a flow chart showing the logic of the diagnostic analysis performed by the processor of the laryngotracheal airway monitor shown in FIG. 1.

FIG. 5 is a flow chart which illustrates the theoretical logic of software run on the CPU 28 that implements the spectra analysis and diagnosis process according to the invention. This software can be implemented in any language (i.e., BASIC, Pascal, etc.) supported by the CPU 28 and a computer programer of ordinary skill in the art based on the flow chart. The process begins in function block 40 by retrieving the spectral data which is stored in digital form in DASD 30. This data is first analyzed in decision block 42 to determine if the data represents a normal spectra. If not, an analysis is made in decision block 44 to determine the presence or absence of a narrow peak below 2 kHz. A "narrow peak" is described as a maxima of amplitude above 200 Hz but below 1.5 kHz, with a bandwidth ($-3$ dB down on either side of the peak) in excess of 200 Hz. If a narrow peak exists, the sample is identified as "supraglottal" and the decision is registered in indicator block 60. Such a peak can be seen in FIG. 4B.

If no narrow peak exists, the process continues to decision block 46 wherein the spectra is examined for a broad peak either below 0.75 kHz or above 1 kHz. A "broad peak" is identified as a region of maximum energy beginning below 150 Hz and with a bandwidth of at least 0.5 kHz. If the broad peak occurs at a point which is less than 0.75 kHz, the sample is identified as "glottic" and registered as such in indicator block 52. Such a spectrum is illustrated in FIG. 4C. If the broad peak extends to above 1 kHz, decision block 46 passes this information to decision block 48. FIGS. 4A and 4D illustrate spectra which would be sent to decision block 48. If no broad peak exists, decision block 46 would route that information to indicator block 58, identified as "normal". Here, "normal" is specified as a "neither" or "none" output, respectively, from decision blocks 46 or 48, with amplitude components at 2.5 kHz at least 30 dB down from the peak value.

Returning now to decision block 48, the decision is whether a secondary peak exists either from 1.5 kHz to 2.0 kHz or from 2.0 kHz to 3 kHz. If the former, then decision block 48 sends the information to indicator block 54 which identifies the spectrum as "oropharyngeal". If the latter, then decision block 48 sends the information to indicator block 56, indicating a "subglottic" obstruction.

Spectra which lead to decisions indicated at blocks 60, 52, 54, and 56 are then led to a stridor detector, represented by block 50. Stridor is operationally defined as a peak below 1 kHz, with a bandwidth of less than 50 Hz and an amplitude greater than 10 dB in comparison to values outside the band. If such a peak is found, block 50 would signal "stridor".

The foregoing discussion has been limited to a consideration of spectra processed using algorithms which in effect "smooth" the spectra, thus eliminating instantaneous noise peaks. Smoothing is accomplished by increasing the integration time for successive FFTs which are averaged together. The discussion has also assumed spectra derived from long-term successive FFT averages. Similar algorithms are used for the three-dimensional spectral, with the addition of a time indicator which would indicate the particular phase of the respiratory cycle during which the events occurred. The three-dimensional algorithms also would be applied as an incremental function, so that several successive analyses would be carried out on a single respiratory cycle. Adding the element of time or respiratory cycle phase will yield greater specificity to the decisions, although they will be more costly in terms of processing time. With increasing speed of microprocessors, however, this likely will be reduced to an acceptable and near "real-time" period in the near future.

Comparison of successive samples are made by first storing processed spectra in digital form in DASD 30, and then recalling specific times by a "dial-up" system which enters spectra into the decision algorithm. Successive graphic readouts can be produced, one on top of the other, to provide a visual comparison for the physician or technician. Improvement in respiratory function would be indicated by a lessening of stridor and a reduction in the amplitude of noise components within the composite displays.

With respect to automatic processing of the data, the simplest decision would be when a patient's spectra changes from one of the patterns indicated in blocks 52, 60, 54, or 56 in FIG. 5 to block 58 or "normal". Changes within each class could be made with another set of algorithms developed to indicate changes in the amplitude of components within each decision block and shifting of frequency components toward the "normal" status.

It will be understood that the logic of the analyses performed by the invention may be refined and enhanced by the addition of other templates. These, for example, might include new patterns which will become apparent with more patient data samples, and adjustment of the decision rules which will produce a more definitive decision, such as greater specificity of resonant peak location and bandwidth. In addition, algorithms for detecting change in successive samples will be added. Use of the pulmonary monitor to indicate respiratory phase will be incorporated into the smoothed sample analyses to provide further indication of supra and subglottal obstruction location.

Alternatively, other pattern recognition algorithms may be used. Such algorithms may be based on Euclidian distance comparisons between stored and contemporary patterns, "best fit" comparisons based on principal components, extremes, and histograms of energy in successive narrow bands, and statistical treatment of the foregoing.

The invention thus described consists of two parts providing, respectively, a data acquisition and graphic readout part and an automated pattern recognition part. The unique portion of the data acquisition and graphic readout part is the use of accelerometers and pulmonary monitors (for breathing phase) as inputs, the normalization of the graphs so that they can be read both within one person and across populations, and the coordination with the automated pattern recognition part to demonstrate what portion of the spectrum or indeed what spectrum was used to make the automatic decisions.

While the invention has been described in terms of a preferred embodiment consisting of two principle parts, those skilled in the art will recognize that the invention can be practiced with modification within the spirit and scope of the appended claims. For example, it is contemplated that a production model of the laryngotracheal airway monitor will employ a special purpose CPU rather than a general purpose PC. Such a special purpose computer may incorporate a microprocessor from the Intel family of microprocessors in the 8086 or 80x86 line of microprocessors to provide compatibility with MS DOS based software, although this is only optional. Other microprocessors, including RISC (reduced instruction set computer) microprocessors and other operating systems may be used in the practice of the invention.

Having thus described my invention, what I claim as new and desire to secure by Letters Patent is as follows:

1. A laryngotracheal airway spectra readout comprising:
    accelerometer means adapted to be placed on the outside of the neck of a patient, said accelerometer means generating a first electrical signal corresponding to the physical vibration of breathing noise;
    pulmonary monitor means adapted to be attached to said patient for generating a second electrical signal corresponding to a phase of the patient's breathing; and
    frequency spectrum analyzer means connected to said accelerometer means and said pulmonary monitor means for analyzing said first and second electrical signals and generating a calibrated and normalized graphic readout.

2. A laryngotracheal airway spectra readout as recited in claim 1 wherein said frequency spectrum analyzer means includes means for performing fast Fourier transform analyses on said first electrical signal and for producing a three-dimensional spectral display.

3. A laryngotracheal airway spectra readout as recited in claim 1 wherein said frequency spectrum analyzer means includes means for performing fast Fourier transform analyses on said first electrical signal and for producing a long-term average display.

4. A laryngotracheal airway spectra readout as recited in claim 1 wherein said frequency spectrum analyzer means includes means for performing fast Fourier transform analyses on said first electrical signal and for producing a three-dimensional spectral display and a long-term average display.

5. A laryngotracheal airway spectra readout as recited in claim 1 further comprising analog to digital conversion means interposed between said accelerometer means and said pulmonary monitor means for converting said first and said second electrical signals to digital codes, said frequency spectrum analyzer means performing fast Fourier transform analyses on said electrical signal and producing a three-dimensional spectral display and a long-term average display.

6. A laryngotracheal airway monitor comprising:
    accelerometer means adapted to be placed on the outside of the neck of a patient, said accelerometer means generating first electrical signal corresponding to the physical vibration of breathing noise;
    analog-to-digital converter means connected to receive said first electrical signal and generating a digitized signal;
    pulmonary monitor means adapted to be attached to said patient for generating a second electrical signal corresponding to a phase of the patient's breathing;
    database means for storing known parameters of normal and abnormal airways;

processor means for receiving said digitized signal and said second electrical signal and for performing an acoustic analysis to generate a digitized spectra, said processor means analyzing said digitized spectra by comparing identified parameters of the spectra with said known parameters in said database means and applying decision algorithms to make diagnoses of location and degree of an airway obstruction based on the comparisons with the stored normal and abnormal parameter data; and readout means connected to said processor means for providing as an output the results of the diagnoses.

7. The laryngotracheal airway monitor as recited in claim 6 wherein records of current breathing analysis are stored in said database means and compared by said processor means as a function of time to ascertain improvement or deterioration of a patient's condition.

8. The laryngotracheal airway monitor as recited in claim 6 wherein said readout means presents the results of the diagnoses graphically.

9. The laryngotracheal airway monitor as recited in claim 6 further comprising alarm means connected to said processor means for providing an alarm if predetermined conditions are detected.

10. A method of monitoring a patient's laryngotracheal airway comprising the steps of:

generating a first electrical signal with an accelerometer placed on the outside of a patient's neck, said electrical signal corresponding to the physical vibration of breathing noise;

converting said electrical signal to a digitized signal;

generating a second electrical signal corresponding to a phase of the patient'breathing;

storing in a database known parameters of normal and abnormal airways;

performing an acoustic analysis with a processor on said digitized signal and said second electrical signal to generate a digitized spectra;

using said processor to analyze said digitized spectra by comparing identified parameters of the spectra with said database of known parameters and applying decision algorithms to make diagnoses of location and degree of an airway obstruction based on the comparisons with the stored normal and abnormal parameter data; and providing as an output of said processor the results of the diagnoses.

11. The method of monitoring a patient's laryngotracheal airway recited in claim 10 further comprising the steps of:

storing records in said database of current breathing analysis; and comparing stored records by said processor as a function of time to ascertain improvement or deterioration of the patient's condition.

* * * * *